(12) United States Patent
Malinin (10) Patent No.: US 9,737,590 B2
(45) Date of Patent: Aug. 22, 2017

(54) SELF-ASSEMBLY OF COLLAGEN FIBERS FROM DERMIS, FASCIA AND TENDON FOR TISSUE AUGMENTATION AND COVERAGE OF WOUNDS AND BURNS

(71) Applicant: Vivex Biomedical, Inc., Marietta, GA (US)

(72) Inventor: Theodore I. Malinin, Key Biscayne, FL (US)

(73) Assignee: Vivex Biomedical, Inc., Atlanta, GA (US)

(*) Notice: Subject to any disclaimer, the term of this patent is extended or adjusted under 35 U.S.C. 154(b) by 412 days.

(21) Appl. No.: 13/955,226

(22) Filed: Jul. 31, 2013

(65) Prior Publication Data

US 2015/0037432 A1    Feb. 5, 2015

(51) Int. Cl.

| A61K 38/00 | (2006.01) |
| A61K 48/00 | (2006.01) |
| A61K 35/12 | (2015.01) |
| A61K 35/34 | (2015.01) |
| A61K 35/36 | (2015.01) |
| A61K 38/39 | (2006.01) |
| A61K 35/32 | (2015.01) |

(52) U.S. Cl.
CPC ........... *A61K 38/39* (2013.01); *A61K 35/32* (2013.01); *A61K 35/36* (2013.01); *Y10T 428/2982* (2015.01)

(58) Field of Classification Search
None
See application file for complete search history.

(56) References Cited

U.S. PATENT DOCUMENTS

| 6,194,182 | B1 | 2/2001 | Tranquillo | |
| 6,287,340 | B1 | 9/2001 | Altman | |
| 6,544,762 | B1 | 4/2003 | Tranquillo | |
| 7,071,001 | B2* | 7/2006 | Brubaker | G01N 33/4905 422/425 |
| 8,460,167 | B2 | 6/2013 | Chornenky | |
| 2006/0105454 | A1 | 5/2006 | Son | |
| 2006/0177492 | A1* | 8/2006 | Yunoki | A61K 9/06 424/445 |
| 2010/0074874 | A1 | 3/2010 | Torbet | |
| 2010/0256774 | A1* | 10/2010 | Wang | A61L 27/3608 623/23.63 |
| 2013/0190480 | A1 | 7/2013 | Nakano | |
| 2013/0323199 | A1* | 12/2013 | Saku | A61L 27/24 424/85.1 |

FOREIGN PATENT DOCUMENTS

| JP | 2006280222 | 10/2006 |
| KR | 20020065755 | 8/2002 |
| WO | 2012114707 | 8/2012 |
| WO | 2013069661 | 5/2013 |

OTHER PUBLICATIONS

X. Cheng et al. Biomaterials 29 (2008) 3278-3288.*
Brochure_PureCol.*
Vitrogen and PureCol Purified Collagen_PRLog_Feb. 2010.*
Xu B., et al, "Experimental and Modeling Study of Collagen Scaffolds with the Effects of Crosslinking and Fiber Alignment", International Journal of Biomaterials, 2011; article ID 172, 389.
Olde Damink L.H.H., et al, "Glutaradehyde as a crosslinking agent for collagen-based biomaterials", Journal of Materiald Science: Materials in Medicine 6, 1995; 6: 460-472.
Fratzl P, "Collagen: Structure and Mechanics, an Introduction", Springer US, New York 2008, pp. 1.
Vader D., et al, "Strain-Induced Alignment in Collagen Gels", PLOS One , Jun. 2009; 4(6) e5902.
Torbert J., et al, "Orthogonal scaffold of magnetically aligned collagen lamellae for corneal stroma reconstruction", Biomaterials, Oct. 28, 2007(29); 4268-4276.
Gasser T.C., et al, "Hyperelastic modeling of arterial layers with distributed collagen fibre orientations", Journal of the Royal Society Interface, 2006; 3:15-35.
Sacks M.S., et al, "Local Mechanical Anisotropy in Human Cranial Dura Mater Allografts", Journal of Biomechanical Engineering; Aug. 1998; 120:541.
Fanelli C., et al, "Magnetic fields increase cell survival by inhibiting apoptosis via modulation of Ca2+ influx", The FASEB Journal, Jan. 1999; 13, 1:95-102.
Kotani H., et al, "Magnetic orientation of collagen and bone mixture", Journal of Applied Physics, 2000: 87:6191-6193.
Miyakoshi J., "The review of cellular effects of a static magnetic field"; Science and Technology of Advanced Materials, 2006; 7:305-307.
Guo C., et al, "Flow and magnetic field induced collagen alignment", Biomaterials 28 (2007) 1105-1114.

(Continued)

*Primary Examiner* — Chris R Tate
*Assistant Examiner* — Douglas F White
(74) *Attorney, Agent, or Firm* — David L. King (57) ABSTRACT

The present invention is a composition of a self-assembly of collagen fibers made from a plurality of sized pieces of a source material. The source material made from animal or human tissue selected from one of dermis, tendon, fascia or dura mater. The self-assembly occurring by induction of a magnetic field in a liquid medium.

20 Claims, 10 Drawing Sheets

(56) References Cited

OTHER PUBLICATIONS

Gaudet, "Characterization of Methacrylated Type 1 Collagen as a Dynamic, Photoactive Hydrogel", Biointerphases 2012 7:25.
Torbet J., et al, "Magnetic alignment of collagen during self-assembly", Biochem J., 1984, 219, 1057-1059.
Barnothy MF, Biologic Effects of Magnetic Fields; Plenum, New York 1968; pp. 25-32.
Whittaker ET, "A History of the Theories of Aether and Electricity"; Dublin University Press Series, New York 1916; pp. 29-30.

* cited by examiner

SELF-ASSEMBLY OF COLLAGEN FIBERS FROM DERMIS, FASCIA AND TENDON FOR TISSUE AUGMENTATION AND COVERAGE OF WOUNDS AND BURNS

TECHNICAL FIELD

The present invention relates to the production of collagen compositions suitable for wound coverage, bone coverage, filling tissue voids and cosmetic augmentation of cutaneous contours.

BACKGROUND OF THE INVENTION

Collagen and collagen matrices find many applications in surgery. They are used as a film, putty, gel and paste. Collagen (usually type 1) scaffolds are commonly used in tissue engineering, wound healing, as neurosegeneration guide substrates, and in reconstructive surgery and dermatology. However, most available preparations have poor biomechanical properties compared to tissues they are intended to replace. For that reason, collagen constructs are subject to laboratory manipulations. The strength of collagen fibrils which under natural conditions is not great, can be increased by covalent crosslinks within and between the constituent collagen molecules. Collagen can self-assemble through an enzymatic formation of intermolecular cross-links leading to a head to tail arrangement within the fiber. Gluteraldehyde is one of the most common reagents for crosslinking collagen from collagen gels.

Collagen gel is a convenient, abundant and commonly used biomatrix in laboratory studies. Collagen used in the laboratory studies is obtainable commercially in large quantities. It is extracted from animal sources by acid hydrolysis, producing acid soluble collagen which has to be neutralized before use.

The mechanical properties of collagen gels have been extensively investigated. In this connection, anisotropic hyperelastic constitutive models are used. These include collagen fiber dispersion. The response of the model captures both an isotropic and anisotropic component. The latter assumes collagen fibers to be active only in extension.

Numerous studies with collagen gels and other purified collagen substances were directed at producing collagen scaffolding. These efforts were largely unsuccessful, primarily because of poor biomechanical characteristics of constructed scaffoldings, compared to structures they were intended to replace.

Clearly something else had to be tried. Not all collagen-containing membranous structures are architecturally alike. Skin dermis is made up of two layers with elastic fibers interspersed among dense collagen fibers. Fascia is made up of parallel collagen columns held together by loose fibrous tissue. Like dermis, fascia lata is composed of two layers. Tendons have relatively few cells and an abundant collagenous material. Dura mater is a specialized structure with collagen fibers oriented in lamina. The architecture of collagen fibers of dura mater is unique compared to other membranous structures. Dura mater collagen presents an anisotropic structure.

Due to the variety of different collagen types and structures and the use of a variety of sources with degrading and harsh methods of cleaning and processing the material, the results with collagen gels and other purified collagen based material needs improvement due to the generally poor results with collagen scaffolding.

One such improvement is in the use of strong magnetic fields.

Magnetic fields and their influence on mammalian cells have been studied over several decades by a number of investigators. There have been numerous attempts to demonstrate significant effects on biologic systems. Magnetic fields were reported to effect cellular metabolism. Unequivocal effect on intact mammalian cells by magnetic fields was demonstrated by Malinin et al in 1976. These investigations showed that strong magnetic fields (5000 oersted) can induce morphologic and physiologic transformations of mammalian cells. They concluded that the transformations were due to magnetic field effects alone. This is important, as subsequently Brighton postulated that the effects of pulsed electromagnetic fields are due to the electric field, and not the magnetic field. The difference between the magnetic and the electric field is, that in a magnetic field force on a charged particle is due to charged particle movement while the force imparted by an electric field on a charged particle is not due to the charged particle's movement. From a practical standpoint, the difference is important. Magnetic fields at commonly employed frequencies penetrate biological systems, including the human body to any depth; electrical fields do not, necessitating placement of electrodes near the object to be effected. In living cells, static magnetic fields decrease cell death by apoptosis. Magnetic control of osteoblast collagen orientation has also been reported.

In non-viable systems of collagen gel, orthogonal scaffold of magnetically aligned collagen had been attempted to provide for substitution of corneal stroma. Strain induced alignment of collagen gels had been reported. Static magnetic field effects on cells of pheochromacytoma cell line demonstrated effect on adenosine receptors. Byphasic nature of collagen gels is used to explain the mechanical behavior of collagen scaffoldings under mechanical stress. Static magnetic fields are reported to have little effect on cells. All of the above cited studies were performed either on living mammalian cells or on collagen gels with collagen of bovine origin subjected to acid hydrolysis or other modes of harsh treatment such as heat.

In the prior art, thermally assisted pulse electromagnetic field stimulation is disclosed in U.S. Pat. No. 8,460,167. The effect on the joint treated by the method described in the embodiments is produced by electric rather than magnetic fields. In a Japanese patent JP2006-280222 entitled, "Magnetic Circuit For Arranging Molecules Such As Collagen And Cell And Apparatus Using The Same", the inventors disclose a magnetic circuit characterized by using a permanent magnet having a generated magnetic field strength of >=2T as a magnetic field-generating source to arrange collagen, cells and the like, and an apparatus using the magnetic circuit. The collagen subjected to the disclosure in this invention was that of osteoblast in cell culture. The magnetic field was of high intensity 2.0 T and 2.5 T derived from permanent magnets. The effect was observed only on mouse osteoblast cells secreting collagen with respect to their orientation. Collagen used was of animal origin in the form of a gel. The disclosures are strikingly different from the embodiments of the present invention. The Hajme invention is based on viable cells and bovine gel collagen.

In WO2013069661, entitled "Vascular Progenitor Cell Sheet Derived From Induced Pluripotent Stem Cells, And Production Method Therefor", the invention addresses the problem of providing a vascular progenitor cell sheet derived from induced pluripotent stem cells, which has the strength to tolerate practical applications and exhibits a high treatment effect. This vascular progenitor cell sheet derived from induced pluripotent stem cells is prepared by performing: (1) a step for preparing magnetically labeled Flk-1 positive cells derived from induced pluripotent stem cells; (2) a step for preparing a mixture of the Flk-1 positive cells and a gel material including type I collagen, laminin, type IV collagen and entactin as active ingredients, and then disseminating the mixture in a culture vessel; (3) a step for drawing the Flk-1 positive cells in the mixture to the culture surface of the culture vessel by application of a magnetic force to form a multi-layered cell layer; and (4) a step for gelling the gel material. The WO2013069661 invention deals with magnetically labeled cells. The method aids in cell separation of animal origin collagen type I and IV used for cell propagation.

In US2010074874, "Synthetic Multi-Layer Structures Comprising Biopolymer Fibres", the invention relates to a method for the preparation of a synthetic multi-layer structure comprising biopolymer fibers, wherein the biopolymer fibers in each layer are unidirectionally and uniformly oriented, which comprises successive polymerization of layers of a biopolymer fiber forming solution in the presence of a magnetic field, wherein the fiber orientation in at least one layer differs from that in at least one of its superior and/or inferior layer according to an angle alpha. The invention also relates to a biological tissue-like multi-layer structure comprising the synthetic multi-layer structure and cells inoculated therein, such as an orthogonal multi-layer collagen and/or fibrin tissue-like cornea, and the method for its preparation. The invention deals with synthetic biopolymer structures.

U.S. Pat. No. 6,194,182, "Magnetically oriented tissue-equivalent and biopolymer tubes", discloses tissue-equivalent and biopolymer tubes which are oriented by a magnetic field. These oriented fibrils provide enhanced mechanical properties to the tissue-equivalent and biopolymer tubes. One such tissue-equivalent tube includes a body of collagen with mammalian tissue cells interspersed therein. The collagen fibrils are circumferentially oriented within the tubular body by a magnetic field, thereby inducing circumferential orientation of the cells. Methods of making magnetically oriented tissue-equivalent tubes and biopolymer tubes are also disclosed. The invention deals primarily with biopolymer tubes loaded with cells and collagen fibrils, not fibers from collagen gels. The type of magnetic field used to orient these is not disclosed. The invention described deals with biopolymers, viable cells and subcellular components of collagen gels of animal origin.

The present invention has the objective of solving these issues of poor collagen scaffolding by a clearly unique combination using human collagen harvested and processed to maximize structural scaffolding.

SUMMARY OF THE INVENTION

The present invention deals with non-viable human collagen fibers and strands and discloses self-assembly of these structures and not only change in orientation of cells in monolayer cell cultures not confined to tissue structures, as is the case in the present invention. While human collagen is preferred, it is expected that animal collagen similarly processed may provide improved scaffolding results as well and therefore this source is not necessarily excluded from the claimed invention. The source of the collagen can be from living specimens or deceased. The treatment and method of preparation and storage makes the use of non-viable (i.e. non-living cells) most practical and convenient.

The findings disclosed in the present invention were derived from the studies with unaltered collagen from human tissues. The treatment they were subjected to was either freeze-drying or hypothermic dehydration. The reason dehydrated tissues were used is that it was found empirically to produce consistently high yields compared to fresh tissue.

Because of poor results with collagen scaffolding prepared from collagen gels and other purified collagen materials, it appeared logical to prepare scaffolding mimicking or modifying the original structures. In treating some of these structures with enzymes in magnetic stirring, the unexpected influence of magnetic fields on collagen in these structures was discovered.

The present invention is a composition of a self-assembly of collagen fibers made from a plurality of sized pieces of a source material. The source material was made from animal or human tissue selected from one of dermis, tendon, fascia or dura mater. The self-assembly occurring by induction of a magnetic field in a liquid medium at a low to medium magnetic field strength, preferably while stirring the material in the liquid medium, the magnetic field being 38 gauss or less, preferably about 17 to 27 gauss exposure for 24 hours.

The source material is freeze-dried, hypothermically dehydrated or chemically dehydrated. The plurality of sized pieces of source material is fabricated to a size varying from 2×2 cm to 50 microns from a processed sheet of the source material. The shape of the plurality of sized pieces of source material is circular, oval, rectangular, rhomboid, multiangular, triangular or other 2 dimensional shaped piece. The composition forms connecting bridges. Induction of new connecting bridges are formed between segregated plurality of pieces of the processed source material of the collagenous tissues wherein the bridges are composed of strands of collagen fibers. The connecting bridges extend from one piece to connect another piece to form an interconnected collagen structure. Attachment of the collagen structure to a Teflon-coated magnetic bar exposes the pieces to a magnetic field. The collagen structure achieves a production of collagen fiber self-assemblies in Trypsin-Versene liquid medium. Alternatively, the collagen structure achieves a production of collagen fiber self-assemblies in Hanks' balanced salt solution or other balanced salt solutions, including lactated Ringer's solution, phosphate buffered saline and saline. In another alternative, the collagen structure achieves a production of collagen fiber self-assemblies in water. The magnetic field is generated by utilization of stationary or rotating magnets and magnetic bars to produce magnetic fields inducing the plurality of sized pieces to form connecting bridges. The composition coalesces the segregated collagenous tissue pieces into single collagenous, malleable and soft structures. The composition may be molded wherein segregated collagenous tissue forms into gelatinous masses, producing jelly, putty or paste consistency without resorting to chemical or harsh physical treatment at normothermic or moderately hypothermic temperatures. Preservation of composition is, preferably, achieved by hypothermic dehydration. The plurality of sized pieces has particle sizes from 50 to 1000 microns. The composition is produced without hydrolysis, treated with acid. The source material is preferably non-viable human tissue of dermis, tendon or fascia and dura mater. The source material is preferably processed into sheets of collagen material of a millimeter or greater thickness, but preferably less than 8 mm in thickness. The thickness being selected to provide a durable sheet easily processed into pieces of smaller sizes.

A method of forming a composition of a self-assembly of collagen fibers comprises the steps of preparing a plurality of pieces of a source material from animal or human from one of dermis, tendon, fascia or dura mater; freeze-drying or hypothermically dehydrating or chemically dehydrating the pieces of source material or sheets of the source material prior to preparing the pieces; rehydrating the pieces in a liquid medium; exposing the pieces in the liquid medium to a magnetic field; and inducing the pieces to form connective bridges. The step of producing the plurality of pieces further comprises cutting or slicing the pieces in sizes from 50 microns to 2×2 cm. The step of cutting further comprises forming the pieces into one or more shapes selected from circular, oval, rectangular, rhomboid, multiangular, triangular or other 2 dimensional shaped piece. The liquid can be Trypsin-Versene. The liquid can also be Hanks' balanced salt solution or other balanced salt solutions, including lactated Ringer's solution, phosphate buffered saline and saline. The liquid can even be water. The method further comprises coalescing the segregated collagenous tissue pieces into single collagenous, malleable and soft structures. The method further comprises the step of molding of segregated collagenous tissues into gelatinous masses, producing jelly, putty or paste consistency without resorting to chemical or harsh physical treatment at normothermic or moderately hypothermic temperatures. The method further comprises preservation of composition achieved by hypothermic dehydration. The plurality of sized pieces has particle sizes from 50 to 1000 microns. The method preferably requires collagen to be produced without hydrolysis, treated with acid.

Definitions

As used herein and in the claims:

"Collagen" means a complex molecule of a family of proteins consisting of amino acids, organic molecules made from carbon, hydrogen, nitrogen and oxygen. Connective tissue consists primarily of collagen. Collagen forms fibrils that provide the structure for fibrous tissue, such as ligaments, tendons and skin.

"Fibril" means a fine fiber.

"Fiber" means one of the filaments composing most of the intercellular matrix of connective tissue.

"Filament" means a thin, flexible thread-like object.

"Strand" means a line consisting of a complex of fibers or filaments that are twisted together to form a thread or a rope or a cable.

"Type 1 collagen" means the most abundant collagen of the human body. It is present in scar tissue, the end product when tissue heals by repair. It is found in tendons, the endomysium of myofibrils and the organic part of bone.

BRIEF DESCRIPTION OF THE DRAWINGS

The invention will be described by way of example and with reference to the accompanying drawings in which.

DETAILED DESCRIPTION OF THE INVENTION

The invention is directed to an unanticipated finding of self-assembly of native collagen fibers from dermis, fascia and tendon. Exposure of freeze-dried or hypothermically dehydrated collagen from these structures to proteolytic enzymes renders the structures pliable and soft. However, when enzymatic treatment was performed with continuous agitation by a magnetic stirrer in a large volume magnetic stirrer apparatus, unexpected events took place. The treated circular, rectangular or odd-shaped collagen fibers which emanate from the structures, on their own, attach themselves to other similar structures or to a magnetic bar. This happens independent of size. If the circular structures are small (less than 2 mm in diameter) the procedure results in the formation of firm collagen matrix which is composed of distinct, but interconnected collagen fibers. The same phenomenon occurs with smaller pieces of collagenous membranes including micronized particles. The newly produced matrix is so structured as to allow easy ingrowth of blood vessels and cellular elements making it suitable for tissue augmentation. The collagen matrix made from small particles is likewise suitable as a vehicle and as a carrier for microparticulate bone (undecalcified and demineralized as well as for microparticulate cartilage).

Figure 14:
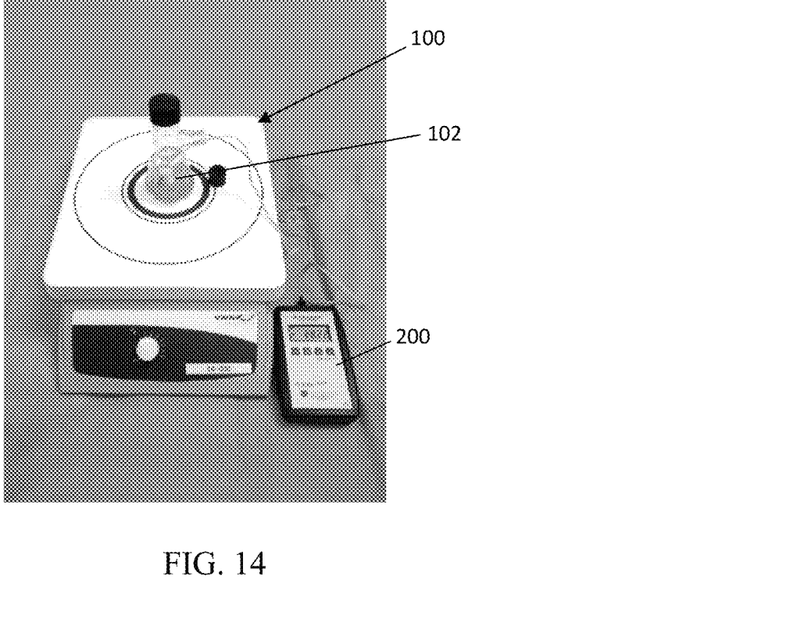
FIG. 14 is a photograph of a magnetic stirrer.

The magnetic field which is responsible for this phenomenon is created by magnetic stir bas 102 and rotating electromagnets of the large volume magnetic stirrer 100. The magnetic field strength or magnetic flux density between the magnetic stirrer 100 magnets and the magnetic bar 102 are of low to moderate intensity, between 15 and 30 Gauss, preferably between 17 and 27 Gauss.

Figure 1:
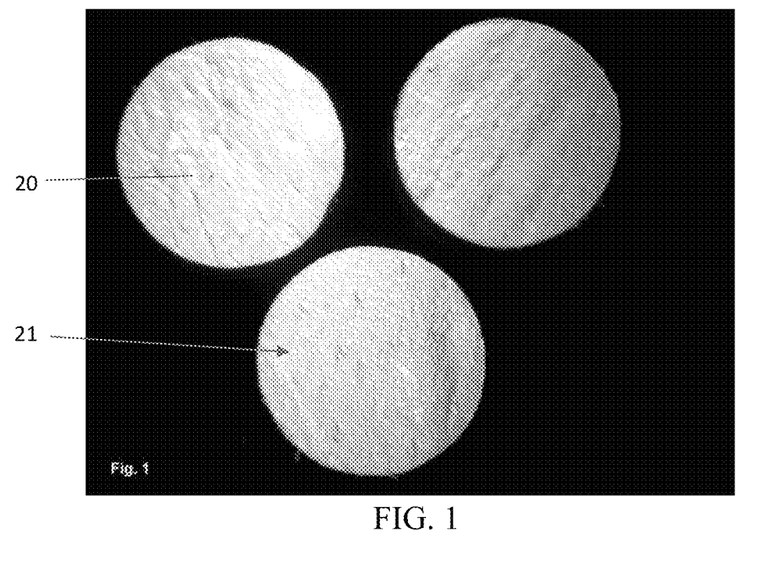
FIG. 1 is a photograph of freeze-dried dermal discs before treatment.
Figure 1A:
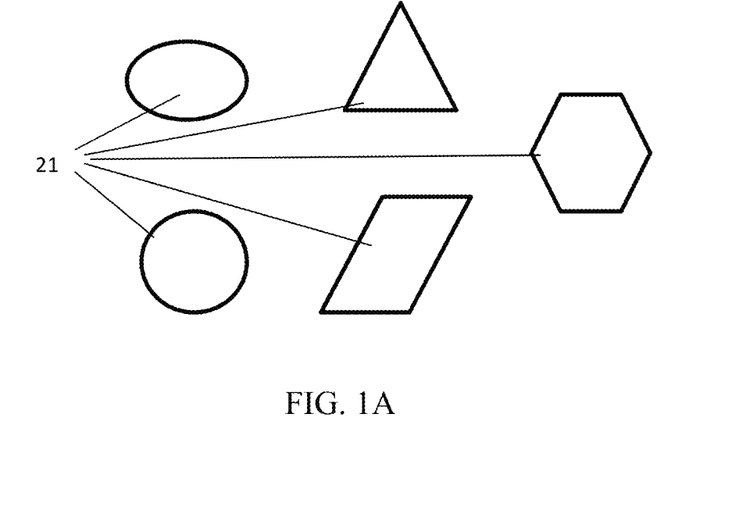
FIG. 1A is an exemplary schematic of the various shapes of the plurality of sized pieces of source material of circular, oval, rectangular, rhomboid, multiangular, triangular or other 2 dimensional shaped piece.

As shown in FIG. 1, 2 mm discs 21 of collagen 20 were cut from freeze-dried decellularized human dermis. Dermis was excised aseptically with a dermatome. Aseptic excision assured absence of bacterial contamination which might have influenced biochemical interactions in the material. Dermis is composed primarily of collagen type I. Dermis was washed and then freeze-dried to a residual moisture of less than 6%. FIG. 1A shows an exemplary schematic of the various shapes of the plurality of sized pieces 21 of source material of circular, oval, rectangular, rhomboid, multiangular, triangular or other 2 dimensional shaped piece.

Figure 2:
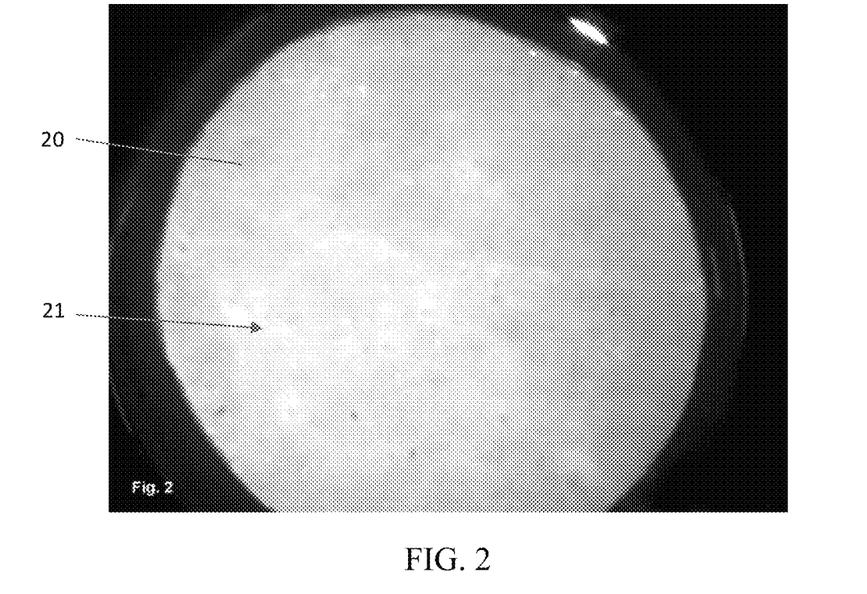
FIG. 2 is a photograph of a freeze-dried dermal disc after a 24 hour exposure to trypsin-versene.
Figure 2A:
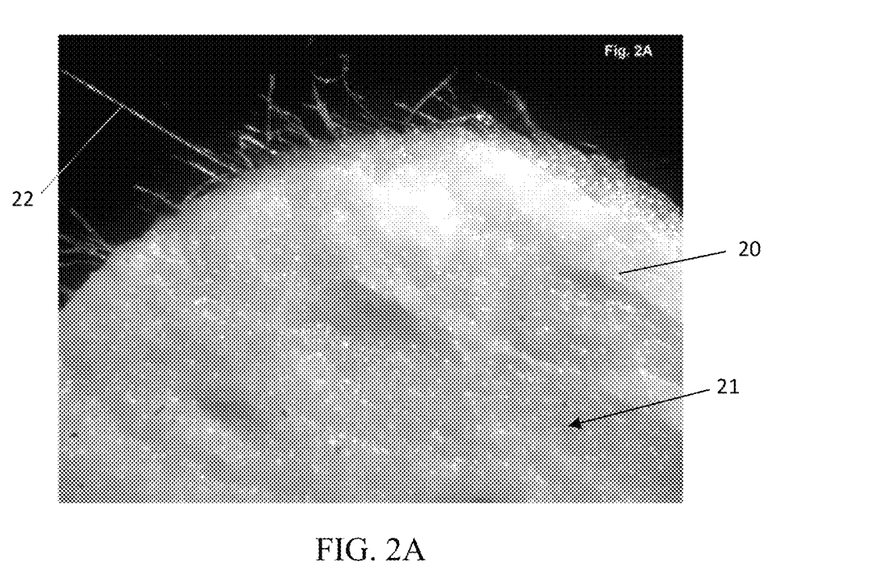
FIG. 2A is a photograph of the dermal disc of FIG. 2A after 24 hour agitation with a magnetic stirrer in trypsin-versene solution.

FIG. 2A shows a freeze-dried dermal disc 21 after 24 hour incubation at room temperature in trypsin-versene solution and agitation with a mechanical propeller. No fiber separation or dissociation of the structure of the dermis took place. FIG. 2B shows the same dermal disc as shown in FIG. 2A, but after 24 hour agitation with a magnetic stirrer in trypsin-versene solution. Collagen fibers 22 visible at edge are escaping from the treated disc 21.

Figure 3A:
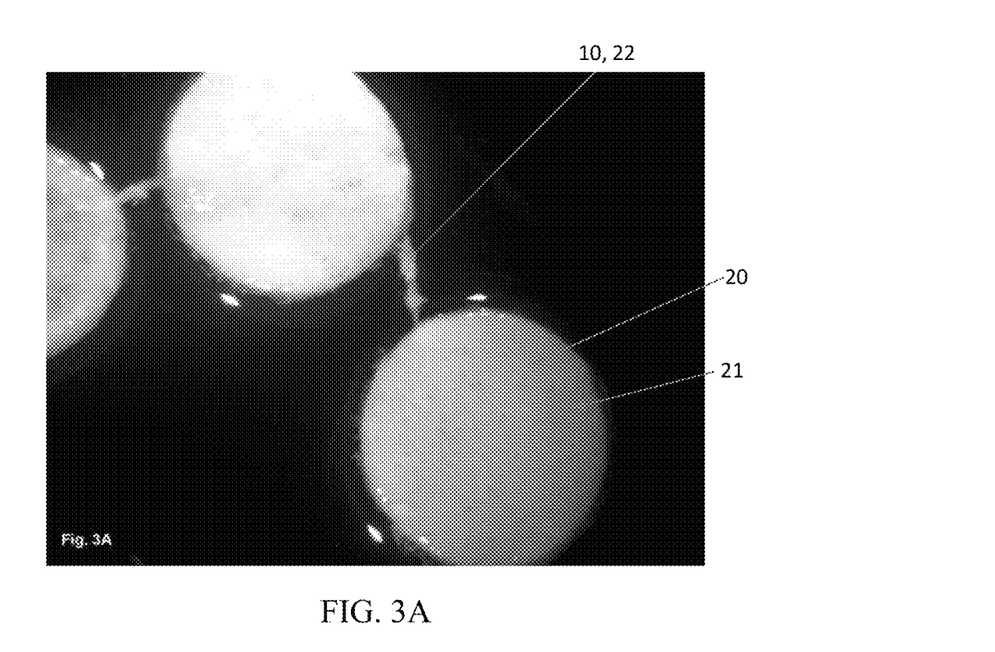
FIG. 3A is a photograph of dermis discs after exposure to a magnetic field; connecting bridges of strands of collagen now connect individual discs.

FIG. 3A shows newly formed bridges of strands 10 of collagen fibers 22 which migrated from disc 21 of the dermis and now interconnect the segregated pieces of tissue.

Figure 3B:
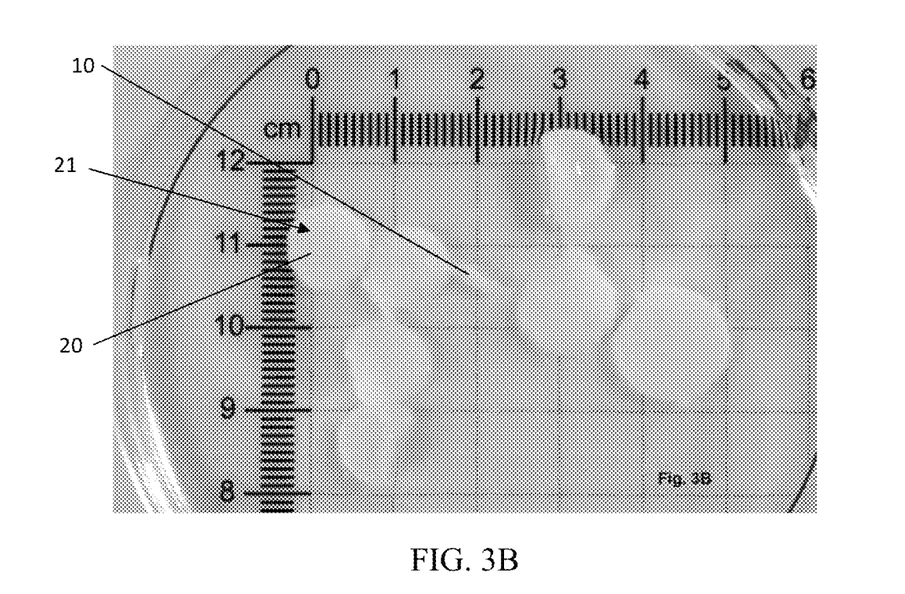
FIG. 3B is a photomicrograph of a collagen bridge showing birefringens of collagen fibers H & E×50.

FIG. 3B is a photomicrograph of a collagen bridge 10 showing birefringence of collagen fibers H & E×50.

Figure 4:
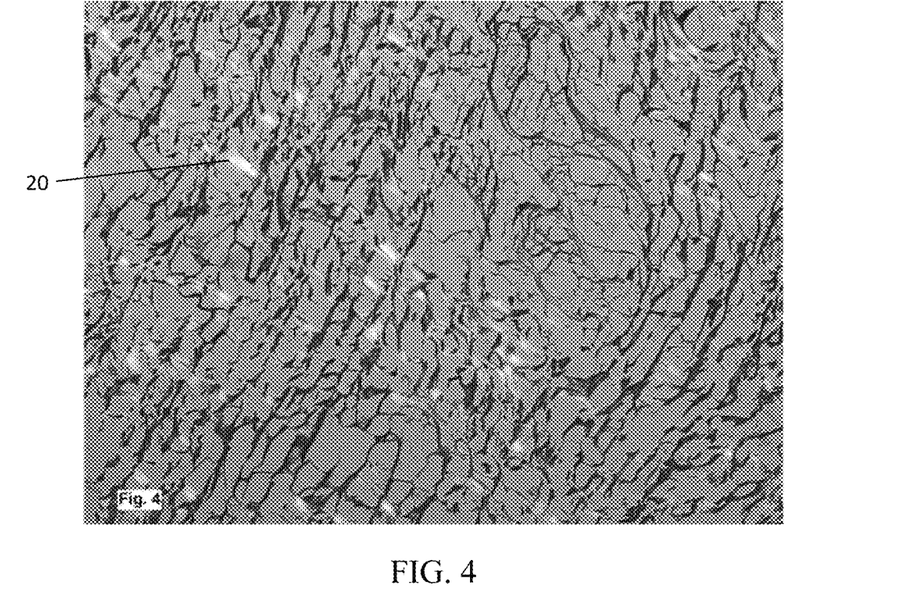
FIG. 4 is a micro-photograph (×100) of dermis treated in a magnetic field. The structure now formed collagen scaffold with separated birefringent collagen fibers.

FIG. 4 shows paraffin embedded tissue sectioned at 5 microns and stained with hematoxylin and eosin. The section is viewed in polarized light with xenon illumation×100. Double refractivity is indicative of collagen 20.

Figure 5A:
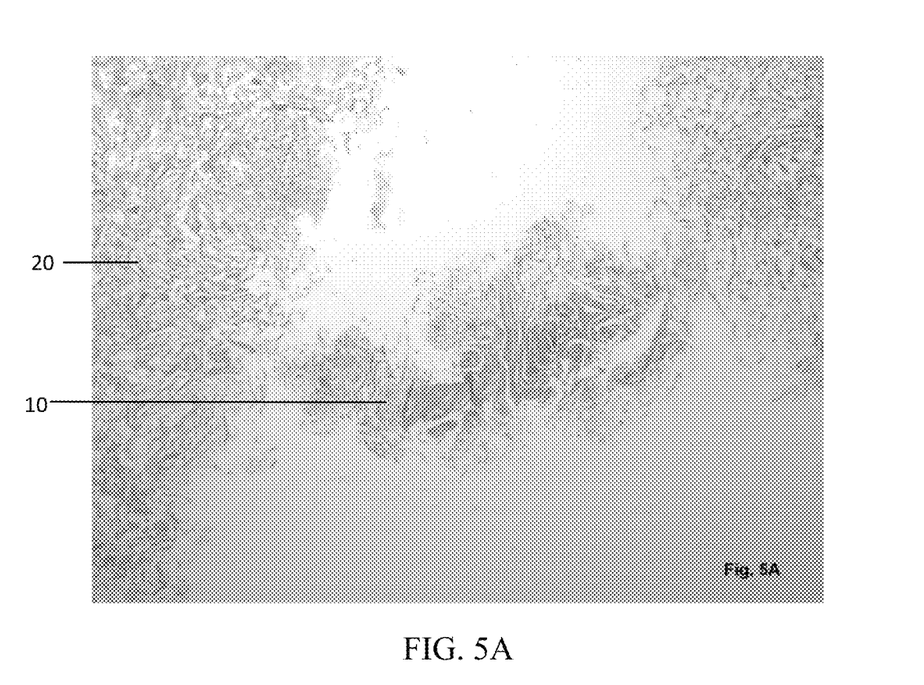
FIG. 5A is a micro-photograph of a newly formed collagen strand connecting two pieces of dermis H & E×50.
Figure 5B:
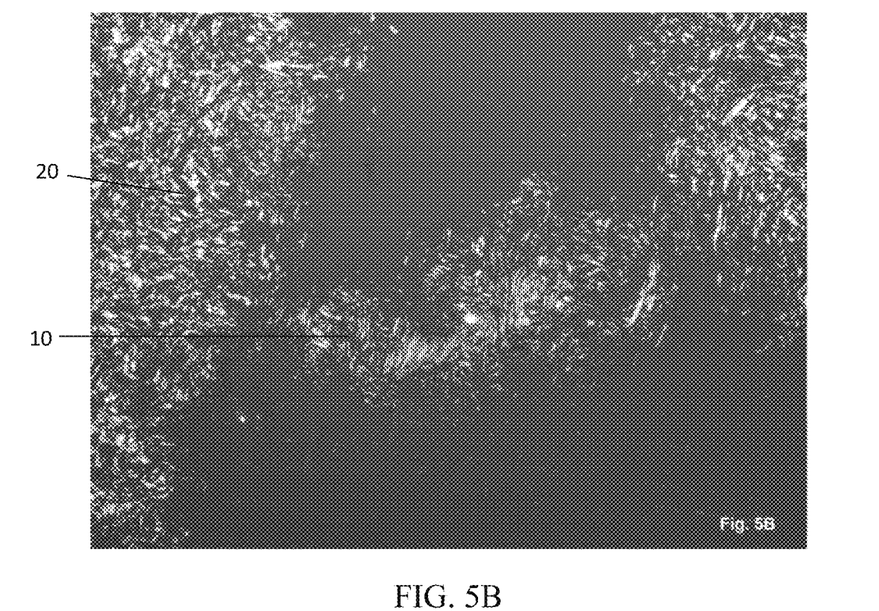
FIG. 5B is a photomicrograph in polarized light of the same collagen bridge as in FIG. 5A.

FIG. 5A shows a microphotograph of a histologic section of a newly formed collagen strand bridge 10 interconnecting two segregated pieces of tissue. Section is stained with hematoxylin and eosin×50. FIG. 5B is polarized light photomicrograph of the same collagen bridge as in FIG. 5A.

Figure 6:
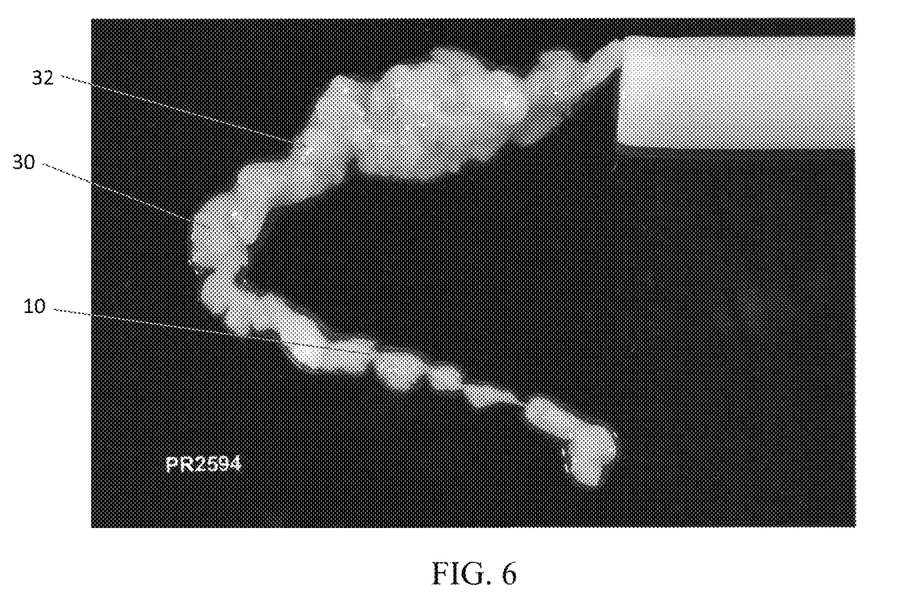
FIG. 6 shows an interconnecting and coalesced section of freeze-dried tendon. One end of the newly formed structure is firmly attached to a magnetic bar.

FIG. 6 shows the tendon collagen 30 self-assembled and arranged in a linear fashion cord-like structure 32 with connecting bridges 10 between masses of collagen reproducing the original structure.

Figure 7:
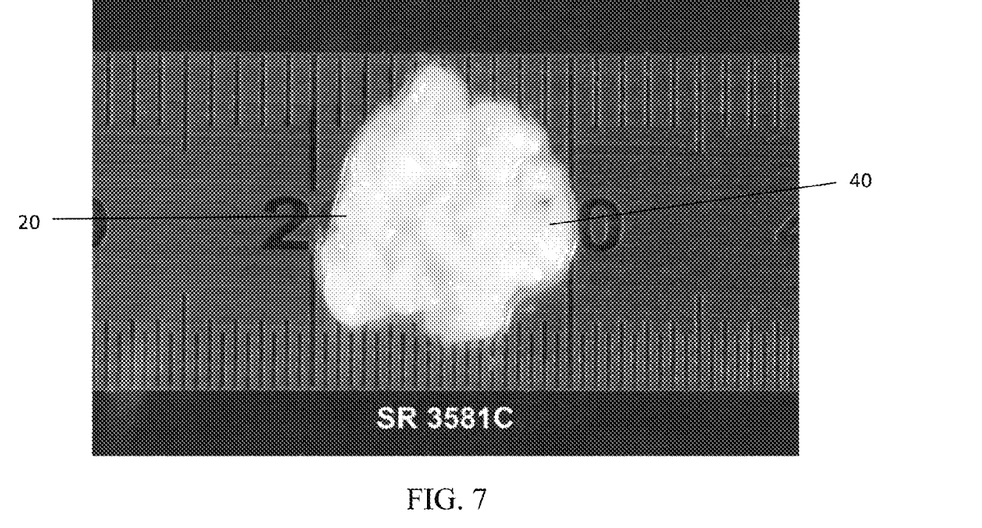
FIG. 7 is a photograph of self-assembled pieces of freeze-dried fascia lata.

FIG. 7. The pieces 21 of self-assembled freeze-dried fascia lata have coalesced forming collagenous scaffolding made of collagen matrix 40.

Figure 8:
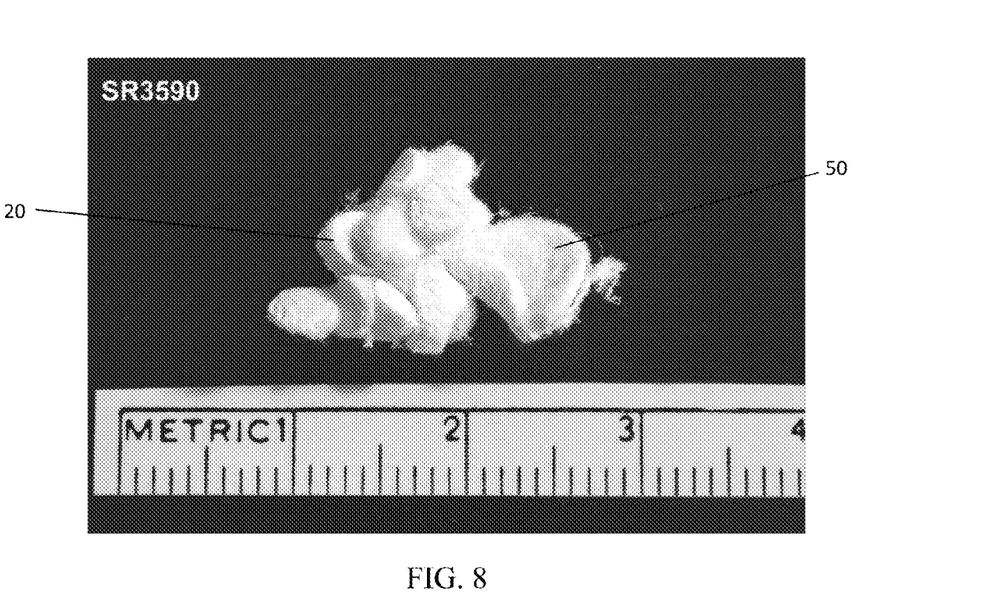
FIG. 8 is a photograph of self-assembled pieces of human dermis preserved by hypothermic preservation.

FIG. 8 shows hypothermic preservation of a human dermis collagen matrix 50 which is not synonymous with freeze-drying as the technique avoids distortion by ice crystals and collapse phenomenon inherent in the freeze-drying process itself.

Figure 9:
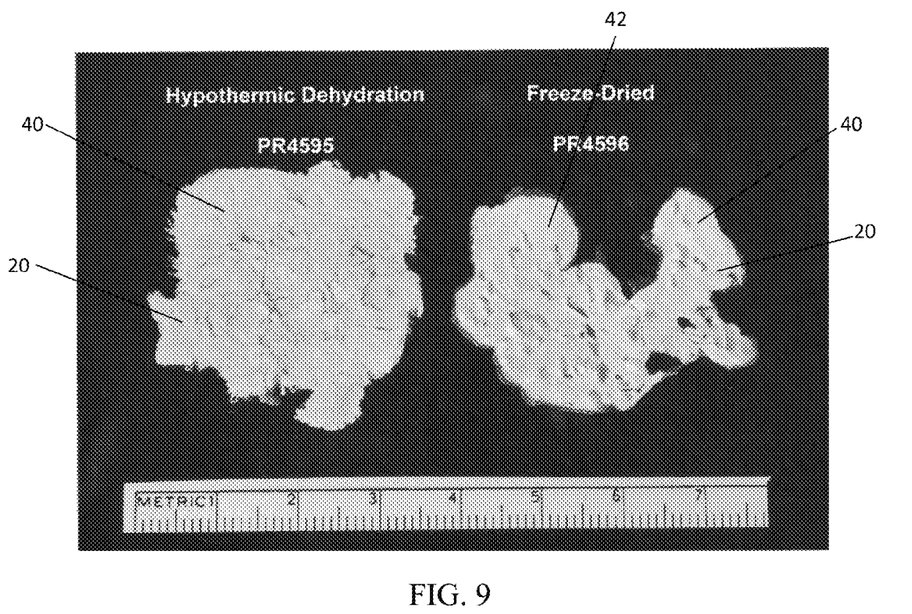
FIG. 9 shows comparison between self-assembled collagen from fascia lata preserved by hypothermic dehydration and by freeze-drying. Freeze-dried preparation has a number of empty spaces created by ice crystals. Hypothermically dehydrated collagen has no such artifacts.

FIG. 9 shows comparison between self-assembled collagen 20 from fascia lata 40 preserved by hypothermic dehydration and by freeze-drying. Freeze-dried preparation has a number of empty spaces 42 created by ice crystals. Self-assembled collagen fibers preserved by hypothermic dehydration has no such artifacts.

Figure 10:
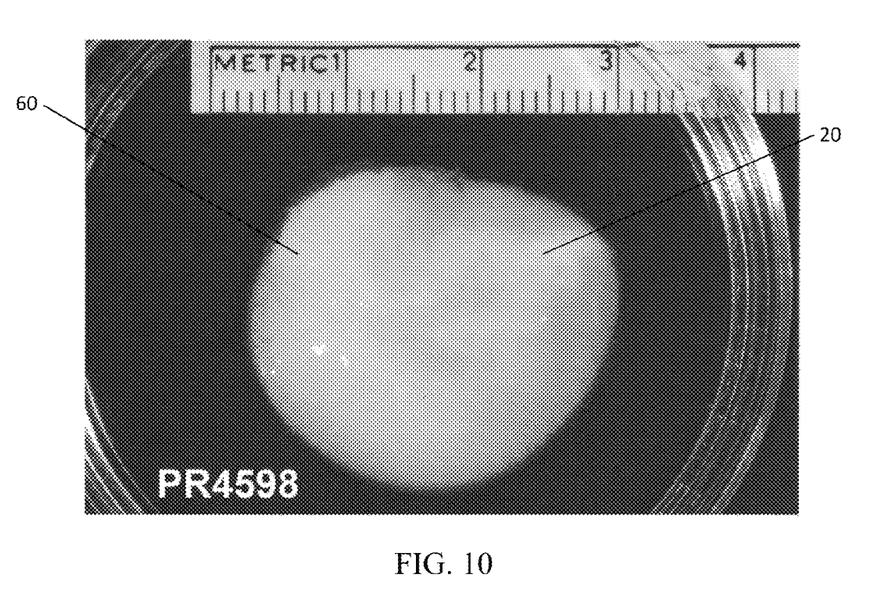
FIG. 10 is a photograph of micronized dermis treated in a magnetic field.
Figure 11:
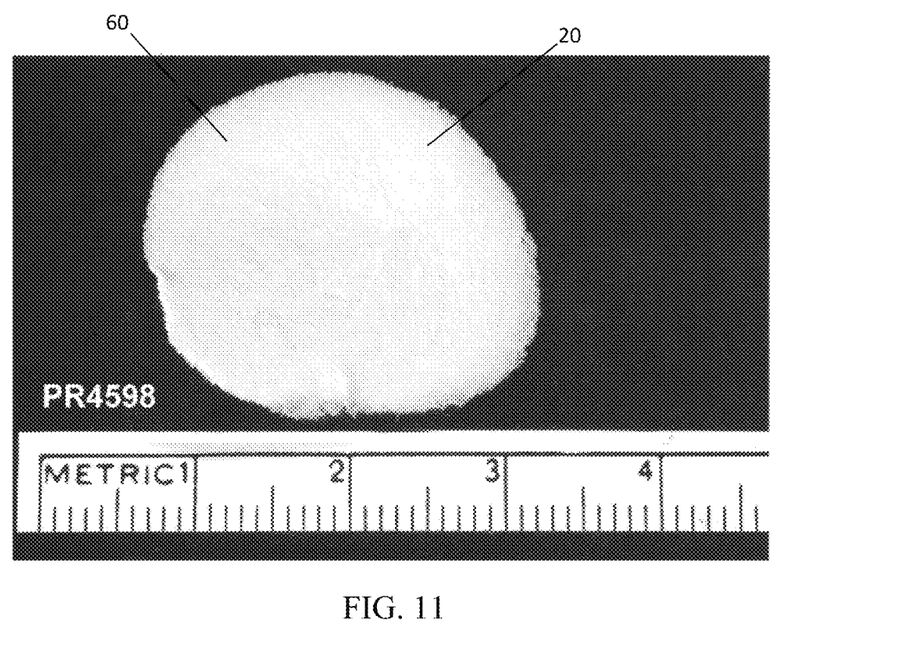
FIG. 11 is a photograph of micronized dermis treated in a magnetic field after preservation by hypothermic dehydration.
Figure 12:
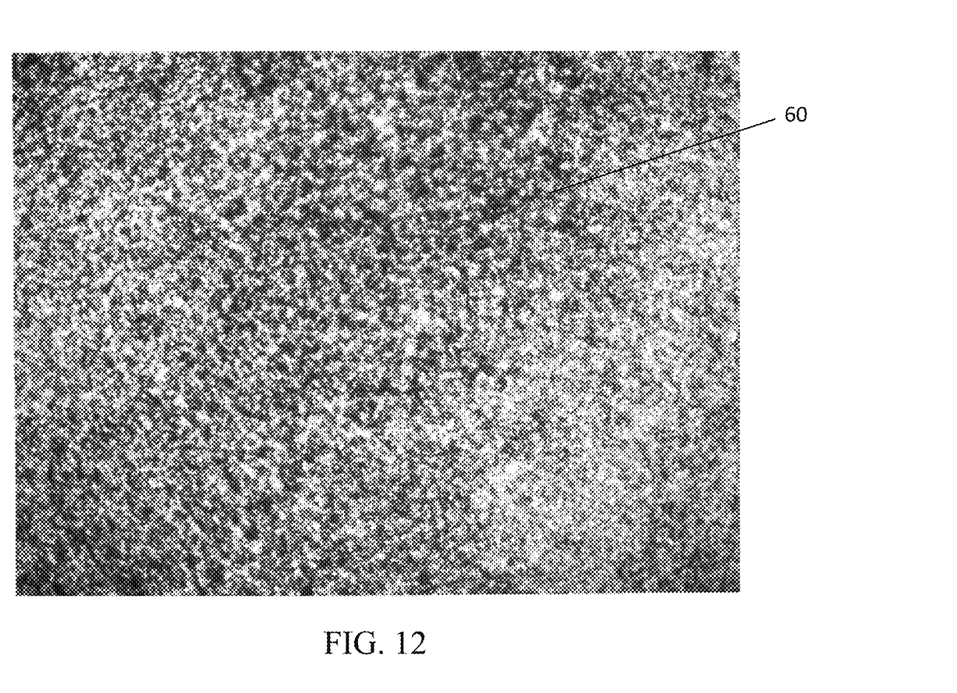
FIG. 12 is a photograph of micronized particles of dermis treated in a magnetic field, as with larger pieces connections between individual particles are visible×10.
Figure 13:
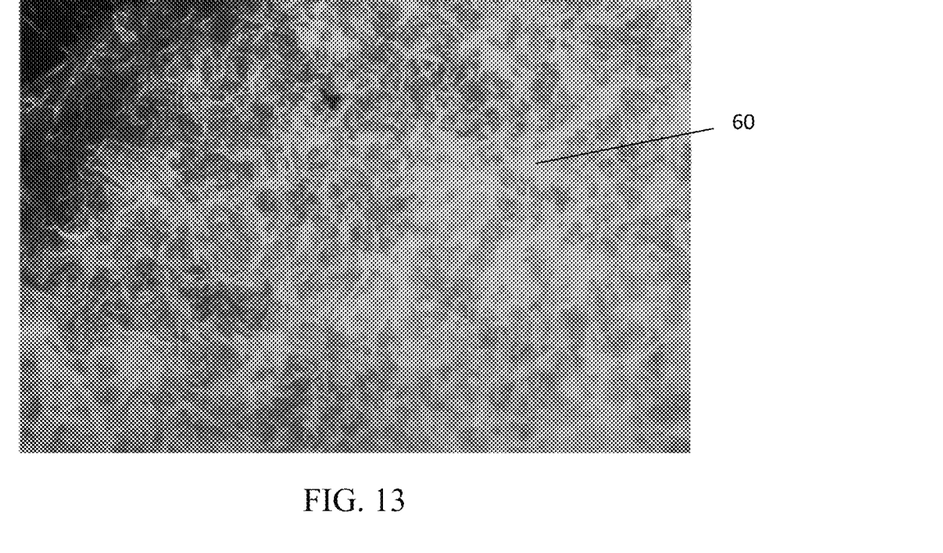
FIG. 13 is a photograph of micronized dermis particles in a fluorescent light. Strands between particles are visible× 100.

FIG. 10 shows the process with micronized particles 60 is basically the same as with larger pieces of tissue. Microparticles 60 disc 21 of collagen 20 up to 3 cm in size diametrically from approximately 100 to 600 microns in size coalesce forming semi-liquid mass which can be used to produce jelly, paste or putty when mixed with mineralized or demineralized bone particles or cartilage particles as shown in FIGS. 10, 11, 12 and 13.

The present inventive composition was exposed to a magnetic induction using a commercially available magnetic stirrer 100. The magnetic stirrer or magnetic mixer 100 shown in FIG. 14 is a laboratory device that employs a rotating magnetic field to cause a stir bar 102 (also called "flea") immersed in a liquid to spin very quickly, thus stirring it. The rotating field may be created either by a rotating magnet or a set of stationary electromagnets, placed beneath the vessel with the composition in the liquid. Since glass does not affect a magnetic field appreciably (it is transparent to magnetism), and the reactions take place in glass vessels, magnetic stir bars 102 as shown in FIG. 14, work well in glass vessels. A gaussmeter 200 is shown in FIG. 14 measuring the magnetic field generated by the magnetic stirrer 100.

Figure 15:
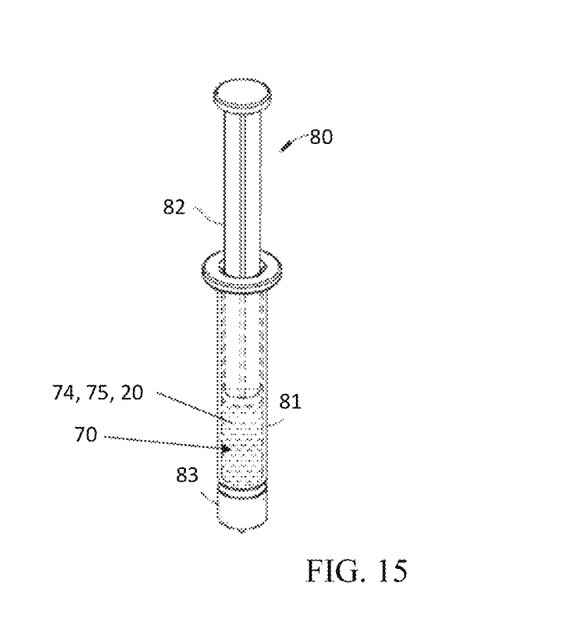
FIG. 15 is a view of a pre-filled syringe with a predetermined amount of the repair mixture in a liquid, preferably saline.
Figure 16:
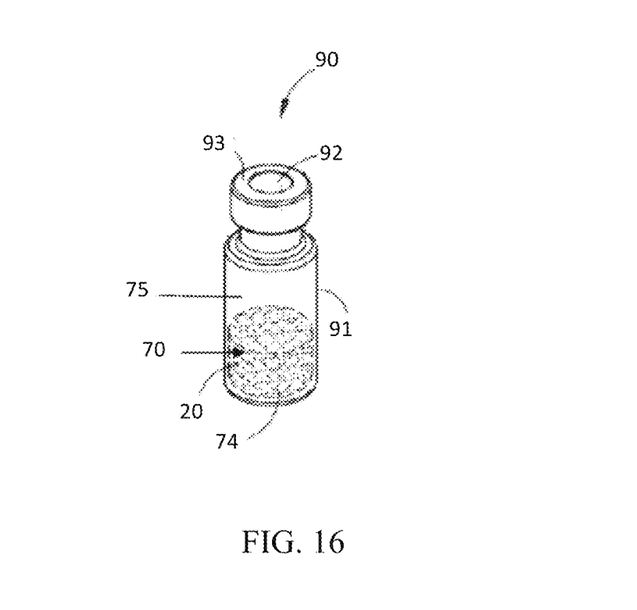
FIG. 16 is a view of a sealed container or vial containing a mixture of bone particles, collagen and saline or other suitable liquid or gel.

As shown in FIGS. 15 and 16, the composition of a bone repair mixture 70 in a pre-filled syringe 80 and a sealed container or vial 90, respectively. The mixture 70 has the bone particles 74 dispersed uniformly in the collagen 20. In either delivery system, the mixture 70 can also be filled with saline or other suitable liquid or gel to facilitate placement in a bone defect or bone cavity prepared for repair.

As shown in FIG. 15, the syringe 80 has a plunger 82 sealed inside the housing 81 closed by a removable cap 83. The plunger 82 is withdrawn to provide volumetric space for the pre-filled mixture 70. Once the cap 83 is removed, a nozzle is exposed to deliver the mixture 70 to the target area.

Alternatively, the entire mixture 70 can be provided in a sealed vial or container 90. An end cap 93 encircles an injectable elastomeric stopper at one end or top of a housing 91. The mixture 70 of bone particles 74 and collagen 20 as well as saline 75 or any other suitable fluid or gel is placed inside the container housing.

A composition of a bone repair mixture 70 according to the present invention is configured to facilitate repair or regeneration of bone at a target repair site. For example, in some embodiments, the composition can be osteoconductive, osteoinductive, or both. In all cases, the composition includes a mixture 70 of bone particles 74 and a biological carrier such as collagen 20 or a collagen mixture.

The source material is made of collagen harvested from animals or humans, but in such a way that the material is not degraded by excessive heat which reduces the collagen material to a gelatinous blob or exposed to harsh acids like those routinely used in animal processing. The use of acid hydrolysis produces acid soluble collagen that is believed to degrade the collagen and reduce its effectiveness. To better appreciate the present invention, a brief explanation of collagen is provided as follows.

The tropocollagen or collagen molecule is a subunit of larger collagen aggregates such as fibrils. At approximately 300 nm long and 1.5 nm in diameter, it is made up of three polypeptide strands (called alpha peptides, see step 2), each possessing the conformation of a left-handed helix (its name is not to be confused with the commonly occurring alpha helix, a right-handed structure). These three left-handed helices are twisted together into a right-handed coil, a triple helix or "super helix", a cooperative quaternary structure stabilized by numerous hydrogen bonds. With type I collagen and possibly all fibrillar collagens if not all collagens, each triple-helix associates into a right-handed super-super-coil referred to as the collagen microfibril. Each microfibril is interdigitated with its neighboring microfibrils to a degree that might suggest they are individually unstable, although within collagen fibrils, they are so well ordered as to be crystalline.

A distinctive feature of collagen is the regular arrangement of amino acids in each of the three chains of these collagen subunits. The sequence often follows the pattern Gly-Pro-X or Gly-X-Hyp, where X may be any of various other amino acid residues. Proline or hydroxyproline constitute about 1/6 of the total sequence. With glycine accounting for 1/3 of the sequence, this means approximately half of the collagen sequence is not glycine, proline or hydroxyproline, a fact often missed due to the distraction of the unusual GX1X2 character of collagen alpha-peptides. The high glycine content of collagen is important with respect to stabilization of the collagen helix as this allows the very close association of the collagen fibers within the molecule, facilitating hydrogen bonding and the formation of intermolecular cross-links. This kind of regular repetition and high glycine content is found in only a few other fibrous proteins, such as silk fibroin. About 75-80% of silk is (approximately) -Gly-Ala-Gly-Ala- with 10% serine, and elastin is rich in glycine, proline, and alanine (Ala), whose side group is a small methyl group. Such high glycine and regular repetitions are never found in globular proteins save for very short sections of their sequence. Chemically reactive side groups are not needed in structural proteins, as they are in enzymes and transport proteins; however, collagen is not quite just a structural protein. Due to its key role in the determination of cell phenotype, cell adhesion, tissue regulation and infrastructure, many sections of its nonproline-rich regions have cell or matrix association/regulation roles. The relatively high content of proline and hydroxyproline rings, with their geometrically constrained carboxyl and (secondary) amino groups, along with the rich abundance of glycine, accounts for the tendency of the individual polypeptide strands to form left-handed helices spontaneously, without any intrachain hydrogen bonding.

Because glycine is the smallest amino acid with no side chain, it plays a unique role in fibrous structural proteins. In collagen, Gly is required at every third position because the assembly of the triple helix puts this residue at the interior (axis) of the helix, where there is no space for a larger side group than glycine's single hydrogen atom. For the same reason, the rings of the Pro and Hyp must point outward. These two amino acids help stabilize the triple helix—Hyp even more so than Pro; a lower concentration of them is required in animals such as fish, whose body temperatures are lower than most warm-blooded animals. Lower proline and hydroxyproline contents are characteristic of cold-water, but not warm-water fish; the latter tend to have similar proline and hydroxyproline contents to mammals. The lower proline and hydroxproline contents of cold-water fish and other poikilotherm animals leads to their collagen having a lower thermal stability than mammalian collagen. This lower thermal stability means that gelatin derived from fish collagen is not suitable for many food and industrial applications.

In nature, viable tropocollagen subunits spontaneously self-assemble, with regularly staggered ends, into even larger arrays in the extracellular spaces of tissues. In the fibrillar collagens, the molecules are staggered from each other by about 67 nm (a unit that is referred to as 'D' and changes depending upon the hydration state of the aggregate). Each D-period contains four plus a fraction collagen molecules, because 300 nm divided by 67 nm does not give an integer (the length of the collagen molecule divided by the stagger distance D). Therefore, in each D-period repeat of the microfibril, there is a part containing five molecules in cross-section, called the "overlap", and a part containing only four molecules, called the "gap". The triple-helices are also arranged in a hexagonal or quasihexagonal array in cross-section, in both the gap and overlap regions.

There is some covalent crosslinking within the triple helices, and a variable amount of covalent crosslinking between tropocollagen helices forming well organized aggregates (such as fibrils). Larger fibrillar bundles are formed with the aid of several different classes of proteins (including different collagen types), glycoproteins and proteoglycans to form the different types of mature tissues from alternate combinations of the same key players. Collagen's insolubility was a barrier to the study of monomeric collagen until it was found that tropocollagen from young animals can be extracted because it is not yet fully crosslinked. However, advances in microscopy techniques (i.e. electron microscopy (EM) and atomic force microscopy (AFM)) and X-ray diffraction have enabled researchers to obtain increasingly detailed images of collagen structure in situ. These later advances are particularly important to better understanding the way in which collagen structure affects cell-cell and cell-matrix communication, and how tissues are constructed in growth and repair, and changed in development and disease. For example using AFM-based nanoindentation it has been shown that a single collagen fibril is a heterogeneous material along its axial direction with significantly different mechanical properties in its gap and overlap regions, correlating with its different molecular organizations in these two regions.

Collagen fibrils/aggregates are arranged in different combinations and concentrations in various tissues to provide varying tissue properties. In bone, entire collagen triple helices lie in a parallel, staggered array. 40 nm gaps between the ends of the tropocollagen subunits (approximately equal to the gap region) probably serve as nucleation sites for the deposition of long, hard, fine crystals of the mineral component, which is (approximately) $Ca10(OH)2(PO4)6$. Type I collagen gives bone its tensile strength.

Collagen has very good tensile strength—it is one of the long fibrous structural proteins that gives cells structure from the outside, as well as supporting the majority of the body's tissues. As an amino acid, collagen is made from the amine ($-NH2$) and carboxylic acid ($-COOH$) functional groups. The main elements of collagen are hydrogen, oxygen, nitrogen, and carbon. Collagen contains three-stranded helical segments of similar structure. The rare abundance of the three amino acids glycine, proline, and hydroxyproline, give collagen its triple-helical structure. The composition of collagen is considered unique given its high hydroxyproline content.

Type I collagen fibrils have enormous tensile strength; that is, such collagen can be stretched without being broken. These fibrils, roughly 50 nm in diameter and several micrometers long, are packed side-by-side in parallel bundles, called collagen fibers, in tendons, where they connect muscles with bones and must withstand enormous forces. Gram for gram, type I collagen is stronger than steel.

The triple-helical structure of collagen arises from an unusual abundance of three amino acids: glycine, proline, and hydroxyproline. These amino acids make up the characteristic repeating motif Gly-Pro-X, where X can be any amino acid. Each amino acid has a precise function. The side chain of glycine, an H atom, is the only one that can fit into the crowded center of a three-stranded helix. Hydrogen bonds linking the peptide bond NH of a glycine residue with a peptide carbonyl ($C=O$) group in an adjacent polypeptide help hold the three chains together. The fixed angle of the C—N peptidyl-proline or peptidyl-hydroxyproline bond enables each polypeptide chain to fold into a helix with a geometry such that three polypeptide chains can twist together to form a three-stranded helix. Interestingly, although the rigid peptidyl-proline linkages disrupt the packing of amino acids in an a helix, they stabilize the rigid three-stranded collagen helix.

Collagen has a wide variety of applications, from food to medical. For instance, it is used in cosmetic surgery and burns surgery. It is widely used in the form of collagen casings for sausages, which are also used in the manufacture of musical strings.

The four collagenous valve rings, the central body of the heart and the extended cardiac skeleton of the heart are histologically and uniquely bound to cardiac muscle. Collagen is the floor of the atria adjoining the ceiling of the ventricles. Collagen contribution to cardiac performance summarily represents an essential, unique and moving solid form of mass opposed to the fluid mechanics of blood mass movement within the heart. The collagenous structure that divides the upper chambers from the lower chambers is an impermeable firewall that excludes both blood and electrical influence through customary anatomical channels. Thanks to collagen, atrial fibrillation almost never deteriorates to ventricular fibrillation. Collagen is infiltrated in varying densities with cardiac muscle mass. The amount (mass), distribution, age and density of collagen all contribute to the compliance required to move blood back and forth. Individual valvular leaflets are held in shape by specialized collagen under variable pressure. Calcium deposition within collagen occurs as a natural consequence of aging. Calcium rich fixed points in a moving display of blood and muscle enable current cardiac imaging technology to arrive at ratios essentially stating blood in cardiac input and blood out cardiac output. Pathology of the collagen underpinning of the heart is closely related to the category Connective Tissue Disease.

According to a study published in the journal Science, oral administration of type II collagen improves symptoms of rheumatoid arthritis. The authors conducted a randomized, double-blind trial involving 60 patients with severe, active rheumatoid arthritis. A decrease in the number of swollen joints and tender joints occurred in subjects fed with chicken type II collagen for 3 months, but not in those that received a placebo. Four patients in the collagen group had complete remission of the disease. No side effects were evident.

A published study reports that ingestion of a novel low molecular weight hydrolyzed chicken sternal cartilage extract, containing a matrix of hydrolyzed type II collagen, chondroitin sulfate, and hyaluronic acid, marketed under the brand name BioCell Collagen, relieves joint discomfort associated with osteoarthritis. A randomized controlled trial (RCT) enrolling 80 subjects demonstrated that BioCell Collagen was well tolerated with no serious adverse event and led to a significant improvement in joint mobility compared to the placebo group on days 35 ($p=0.007$) and 70 ($p<0.001$).

Collagen has been widely used in cosmetic surgery, as a healing aid for burn patients for reconstruction of bone and a wide variety of dental, orthopedic and surgical purposes. Both human and bovine collagen is widely used as dermal fillers for treatment of wrinkles and skin aging. Some points of interest are:

When used cosmetically, there is a chance of allergic reactions causing prolonged redness; however, this can be virtually eliminated by simple and inconspicuous patch testing prior to cosmetic use, and Most medical collagen is derived from young beef cattle (bovine) from certified BSE-free animals. Most manufacturers use donor animals from either "closed herds", or from countries which have never had a reported case of BSE such as Australia, Brazil and New Zealand.

Porcine (pig) tissue is also widely used for producing collagen sheet for a variety of surgical purposes.

Alternatives using the patient's own fat, hyaluronic acid or polyacrylamide gels which are readily available.

As the skeleton forms the structure of the body, it is vital that it maintains its strength, even after breaks and injuries. Collagen is used in bone grafting as it has a triple helical structure, making it a very strong molecule. It is ideal for use in bones, as it does not compromise the structural integrity of the skeleton. The triple helical structure of collagen prevents it from being broken down by enzymes, it enables adhesiveness of cells and it is important for the proper assembly of the extracellular matrix.

Collagen scaffolds are used in tissue regeneration, either in sponges, thin sheets or gels. Collagen has the correct properties for tissue regeneration such as pore structure, permeability, hydrophilicity and it is stable in vivo. Collagen scaffolds are also ideal for the deposition of cells, such as osteoblasts and fibroblasts and once inserted, growth is able to continue as normal in the tissue.

Collagens are widely employed in the construction of artificial skin substitutes used in the management of severe burns. These collagens may be derived from bovine, equine or porcine, and even human sources and are sometimes used in combination with silicones, glycosaminoglycans, fibroblasts, growth factors and other substances.

Collagen is also sold as a pill commercially as a joint mobility supplement with poor references. Because proteins are broken down into amino acids before absorption, there is no reason for orally ingested collagen to affect connective tissue in the body, except through the effect of individual amino acid supplementation.

Collagen is also frequently used in scientific research applications for cell culture, studying cell behavior and cellular interactions with the extracellular environment.

Collagen is one of the body's key natural resources and a component of skin tissue that can benefit all stages of the wound healing process. When collagen is made available to the wound bed, closure can occur. Wound deterioration, followed sometimes by procedures such as amputation, can thus be avoided.

Collagen is a natural product, therefore it is used as a natural wound dressing and has properties that artificial wound dressings do not have. It is resistant against bacteria, which is of vital importance in a wound dressing. It helps to keep the wound sterile, because of its natural ability to fight infection. When collagen is used as a burn dressing, healthy granulation tissue is able to form very quickly over the burn, helping it to heal rapidly.

Throughout the 4 phases of wound healing, collagen performs the following functions in wound healing:

Guiding function: Collagen fibers serve to guide fibroblasts. Fibroblasts migrate along a connective tissue matrix.

Chemotactic properties: The large surface area available on collagen fibers can attract fibrogenic cells which help in healing.

Nucleation: Collagen, in the presence of certain neutral salt molecules, can act as a nucleating agent causing formation of fibrillar structures. A collagen wound dressing might serve as a guide for orienting new collagen deposition and capillary growth.

Hemostatic properties: Blood platelets interact with the collagen to make a hemostatic plug.

If collagen is sufficiently denatured, e.g. by heating, the three tropocollagen strands separate partially or completely into globular domains, containing a different secondary structure to the normal collagen polyproline II (PPII), e.g. random coils. This process describes the formation of gelatin, which is used in many foods, including flavored gelatin desserts. Besides food, gelatin has been used in pharmaceutical, cosmetic, and photography industries. From a nutritional point of view, collagen and gelatin are a poor-quality sole source of protein since they do not contain all the essential amino acids in the proportions that the human body requires—they are not 'complete proteins' (as defined by food science, not that they are partially structured). Manufacturers of collagen-based dietary supplements claim that their products can improve skin and fingernail quality as well as joint health. However, mainstream scientific research has not shown strong evidence to support these claims. Individuals with problems in these areas are more likely to be suffering from some other underlying condition (such as normal aging, dry skin, arthritis etc.) rather than just a protein deficiency.

From the Greek for glue, kolla, the word collagen means "glue producer" and refers to the early process of boiling the skin and sinews of horses and other animals to obtain glue. Collagen adhesive was used by Egyptians about 4,000 years ago, and Native Americans used it in bows about 1,500 years ago. The oldest glue in the world, carbon-dated as more than 8,000 years old, was found to be collagen—used as a protective lining on rope baskets and embroidered fabrics, and to hold utensils together; also in crisscross decorations on human skulls. Collagen normally converts to gelatin, but survived due to the dry conditions. Animal glues are thermoplastic, softening again upon reheating, and so they are still used in making musical instruments such as fine violins and guitars, which may have to be reopened for repairs—an application incompatible with tough, synthetic plastic adhesives, which are permanent. Animal sinews and skins, including leather, have been used to make useful articles for millennia.

Gelatin-resorcinol-formaldehyde glue (and with formaldehyde replaced by less-toxic pentanedial and ethanedial) has been used to repair experimental incisions in rabbit lungs.

The present invention of this collagen composition can be combined with bone particles, preferably bone particles with an improved osteogenic capacity or osteoinductive activity for use in repairing bone defects. In an earlier co-invention of the inventor entitled, "Transplantable particulate bone composition having high osteoinductive capacity and methods for making and using same" provided a very improved use of allograft bone particles.

In that bone particle composition a particulate bone composition with improved osteogenic capacity or osteoinductive activity was discovered.

It provided a particulate bone composition including a particle size distribution of nascent bone particles, allograft bone particles or mixtures or combinations where the particles have a particle size less than or equal to about 355.mu., where .mu. means microns ($1 \times 10^{-6}$ m) of an undemineralized, freeze-dried particulate bone composition and preferably had a distribution of particles having particles sizes between 355.mu. and 250.mu., between 250.mu., and 150.mu. and below 150.mu.

The method used to prepare the bone particles included the step of commutating or grinding of bone to form the particulate bone preparations of this invention, where the commutating or grinding is performed under conditions to ensure that a temperature of the bone being ground does not rise above a critical temperature that would reduce, diminish or eliminate its osteoinductive capacity or activity.

The non-demineralized cortical bone, cancellous bone or mixtures or combinations thereof having a desired particle size distribution included the step of commutating frozen or freeze-dried bone for a time and at a temperature sufficient to produce the desired particle size distribution, where the temperature is below a critical temperature known to be detrimental to an osteogenic capacity or osteoinductive activity of bone. The critical temperature is between about 45 degrees C. to about 50 degrees C., which significantly reduces or completely eliminates osteoinductive properties of bone. The commutating step of this invention includes a defined interruption of grinding so that the temperature to which the bone is exposed is carefully controlled so that the temperature of the bone is kept below the critical temperature which would result in a loss of osteoinductive activity. The mill grinder is preferably operated in cycles of about 8 seconds to about 18 seconds. The bone is then sieved for about 14 seconds to about 15 seconds or longer. This allows for sufficient cooling and for the removal of particles having the desired particle sizes according to the compositions of this invention. This method of defined interrupted commutating does not allow the temperature of bone or grinder to rise above about 33 degrees C. from the initial temperature of the bone which is between about 18 degrees C. and about 20 degrees C. The defined interruption process cycle operates for no longer than 3 minutes with an average operating time of about 2.5 minutes being preferred. However, shorter or longer cycles can be employed provided of course that a temperature of the bone and grinder does not rise to or above the critical temperature, which is preferably set at less than or equal to 40 degrees C., particularly, less than or equal to 35 degrees C. and especially less than or equal to 33 degrees C.

Combining these two compositions greatly enhances the performance of both materials as it relates to bone defect repair.

While it is understood the collagen matrix produced by the present invention is a significant breakthrough in collagen gel preparation, matrix and scaffolding; but when combined with bone particles, it provides a unique combination for repairing bone defects. It is appreciated that the preferred bone particle composition as the one described above is preferred, it is believed the collagen composition of the present invention will provide improved performance over any other bone particle composition used for similar purposes.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A composition comprising sheets of segregated collagenous tissue pieces, wherein said sheets are formed by a process comprising:
   preparing a plurality of segregated sized pieces of a source material made from unaltered animal or human collagenous tissue selected from the group consisting of dermis, tendon, fascia, and dura mater;
   dehydrating the plurality of segregated sized pieces of source material;
   rehydrating the dehydrated pieces in a liquid medium selected from the group comprising Trypsin-Versene liquid medium, a balanced salt solution, Hanks' balanced salt solution, lactated Ringer's solution, and phosphate buffered saline and saline;
   exposing the rehydrated pieces in the liquid medium to a magnetic field under conditions sufficient to induce the rehydrated pieces to form connecting bridges, without being treated with acid hydrolysis or enzymes, wherein the connecting bridges extend from one source piece to connect another source piece so as to form a self-assembly of collagen fibers as an interconnected collagen structure, whereby the segregated collagenous tissue pieces are coalesced into single collagenous malleable soft structures; and
   forming the collagenous malleable soft structures into sheets having a thickness of one millimeter or greater.

2. The composition of claim 1 wherein the shape of the plurality of sized pieces of source material is circular, oval, rectangular, rhomboid, multiangular, triangular or other 2 dimensional shaped piece.

3. The composition of claim 1 wherein the interconnected collagen structure magnetically adheres to a Teflon-coated magnetic bar.

4. The composition of claim 1 wherein dehydration is achieved by hypothermic dehydration.

5. The composition of claim 1 wherein the plurality of sized pieces has particle sizes from 50 to 1000 microns.

6. The composition of claim 1 wherein the source material is non-viable human tissue of dermis, tendon or fascia and dura mater.

7. The composition of claim 1 wherein the magnetic field is generated by utilization of stationary or rotating magnets and magnetic bars to produce magnetic fields inducing the plurality of sized pieces to induce the formation of new connecting bridges.

8. The composition of claim 7 wherein the plurality of sized segregated pieces exposed to the magnetic field induces the formation of the new connecting bridges between separate pieces into self-assembles of a single collagenous, malleable and soft structures.

9. The composition of claim 7 molding of segregated collagenous tissues into gelatinous masses, producing jelly, putty or paste consistency without resorting to chemical or harsh physical treatment at normothermic or moderately hypothermic temperatures.

10. The composition of claim 1 wherein the magnetic field strength is low to medium.

11. The composition of claim 10 wherein the magnetic field strength is less than 38 gauss.

12. The composition of claim 11 wherein the magnetic field strength is 17 to 27 gauss over a 24 hour exposure.

13. A method of making a composition comprising sheets of segregated collagenous tissue pieces, wherein said method comprises:
    preparing a plurality of segregated sized pieces of a source material made from unaltered animal or human collagenous tissue selected from the group consisting of dermis, tendon, fascia, and dura mater;
    dehydrating the plurality of segregated sized pieces of source material;
    rehydrating the dehydrated pieces in a liquid medium selected from the group comprising Trypsin-Versene liquid medium, a balanced salt solution, Hanks' balanced salt solution, lactated Ringer's solution, and phosphate buffered saline and saline;
    exposing the rehydrated pieces in the liquid medium to a magnetic field under conditions sufficient to induce the rehydrated pieces to form connecting bridges, without being treated with acid hydrolysis or enzymes, wherein the connecting bridges extend from one source piece to connect another source piece so as to form a self-assembly of collagen fibers as an interconnected collagen structure, whereby the segregated collagenous tissue pieces are coalesced into single collagenous malleable soft structures; and
    forming the collagenous malleable soft structures into sheets having a thickness of one millimeter or greater.

14. The method of claim 13 wherein the liquid is Trypsin-Versene.

15. The method of claim 13 wherein the liquid is Hanks' balanced salt solution or other balanced salt solutions, including lactated Ringer's solution, phosphate buffered saline and saline.

16. The method of claim 13 wherein the liquid is water.

17. The method of claim 13 wherein dehydration is achieved by hypothermic dehydration.

18. The method of claim 13 wherein the plurality of sized pieces have particle sizes from 50 to 1000 microns.

19. The method of claim 13 wherein preparing the plurality of pieces further comprises cutting or slicing the pieces into sizes from 50 microns to 2×2 cm.

20. The method of claim 19 wherein said cutting comprises cutting the pieces into one or more shapes selected from circular, oval, rectangular, rhomboid, ultiangular, triangular or other 2 dimensional shaped pieces.

* * * * *